US012721925B2

(12) United States Patent
Almeida

(10) Patent No.: US 12,721,925 B2
(45) **Date of Patent: *Sep. 1, 2026**

(54) STERILIZATION MASK WITH UVC REFLECTIVE CHAMBER AND INTERNAL AND EXTERNAL LIGHTING

(71) Applicant: Lumen Hygienic LLC, Clearwater, FL (US)

(72) Inventor: Stephen Almeida, Clearwater, FL (US)

( * ) Notice: Subject to any disclaimer, the term of this patent is extended or adjusted under 35 U.S.C. 154(b) by 446 days.

This patent is subject to a terminal disclaimer.

(21) Appl. No.: 18/539,510

(22) Filed: Dec. 14, 2023

(65) Prior Publication Data

US 2024/0108779 A1 Apr. 4, 2024

Related U.S. Application Data

(63) Continuation-in-part of application No. 18/321,148, filed on May 22, 2023, now Pat. No. 12,642,881, which is a continuation-in-part of application No. 17/394,539, filed on Aug. 5, 2021, now Pat. No. 11,690,929, which is a continuation-in-part of application No. PCT/US2020/052495, filed on Sep. 24, 2020, and a continuation-in-part of application No. 16/898,679, filed on Jun. 11, 2020, now abandoned.

(51) Int. Cl.

| | |
|---|---|
| ***A61L 9/20*** | (2006.01) |
| ***A62B 18/02*** | (2006.01) |
| ***A62B 23/02*** | (2006.01) |

(52) U.S. Cl.

CPC ................ *A61L 9/20* (2013.01); *A62B 18/02* (2013.01); *A62B 23/02* (2013.01); *A61L 2209/111* (2013.01); *A61L 2209/12* (2013.01); *A61L 2209/14* (2013.01)

(58) Field of Classification Search

CPC .. A61L 9/20; A61L 2209/111; A61L 2209/12; A61L 2209/14; A62B 18/02; A62B 23/02; A62B 18/006; A62B 18/08

See application file for complete search history.

(56) References Cited

U.S. PATENT DOCUMENTS

| | | |
|---|---|---|
| 4,886,056 A | 12/1989 | Simpson |
| 5,165,395 A | 11/1992 | Ricci |
| 5,698,866 A | 12/1997 | Doiron et al. |
| 6,171,548 B1 | 1/2001 | Rose |

(Continued)

*Primary Examiner* — Brendan A Hensel

(74) *Attorney, Agent, or Firm* — Distinct Patent Law; Justin P. Miller

(57) ABSTRACT

The sterilization mask with UVC reflective chamber includes a chamber with reflective liner, through which inhaled and exhaled air passes. The reflective chamber is also referred to as a sterilization chamber. Using a reflective chamber ensures each photon of UVC light has a long life, thus dissipating slowly. Increasing the life of the UVC photons decreases the quantity of photons that must be created. Thus, less power is required to achieve the sterilization. In addition to the internal light sources for sterilization, external light sources provide indication of breathing, and/or external visible lighting to take the place of a headlamp. The position of the external light at the face of the mask, the mask worn over the mouth and nose, places the light closer to the relevant work surface to avoid shadowing and increase like intensity.

13 Claims, 12 Drawing Sheets

(56) References Cited

U.S. PATENT DOCUMENTS

| | | | | |
|---|---|---|---|---|
| 6,257,235 | B1 | 7/2001 | Bowen | |
| 8,252,099 | B2 | 8/2012 | Worrilow | |
| 8,584,676 | B2 | 11/2013 | Gossweiler | |
| 8,733,356 | B1 | 5/2014 | Roth | |
| 10,335,618 | B2 | 7/2019 | Zhou et al. | |
| 11,690,929 | B2 * | 7/2023 | Almeida | A62B 23/02 128/863 |
| 2007/0101867 | A1 | 5/2007 | Hunter et al. | |
| 2007/0163588 | A1 | 7/2007 | Hebrank et al. | |
| 2009/0205664 | A1 | 8/2009 | Lyon | |
| 2010/0128901 | A1 | 5/2010 | Herman | |
| 2012/0279503 | A1 | 11/2012 | Zhou et al. | |
| 2017/0202988 | A1 | 7/2017 | Clark | |
| 2021/0330853 | A1 * | 10/2021 | Mizandari | A62B 7/10 |

* cited by examiner

STERILIZATION MASK WITH UVC REFLECTIVE CHAMBER AND INTERNAL AND EXTERNAL LIGHTING

CROSS-REFERENCE TO RELATED APPLICATION

This application is a continuation-in-part of U.S. patent application Ser. No. 18/321,148, filed May 22, 2023, titled Sterilization mask with UVC reflective chamber and heat dissipation mechanism, which claims priority to:

- U.S. patent application Ser. No. 17/394,539, filed Aug. 5, 2021, titled Sterilization mask with UVC reflective chamber; which was a continuation-in-part of two applications:
  - Application PCT/US20/52495, filed Sep. 24, 2020, titled UVC anti-microbial breathing sterilizing modules, masks, and devices; and
  - U.S. patent application Ser. No. 16/898,679, filed Jun. 11, 2020, titled UVC anti-microbial breathing sterilizing modules, masks, and devices, which was the non-provisional of U.S. Patent Application 62/985,155, filed Mar. 4, 2020, titled UVC Anti-microbial mask and modules.

FIELD

This invention relates to the field of air sterilization and more particularly to a portable device for sterilizing air with integrated light source.

BACKGROUND

Sanitizing air is critical to preventing the spread of airborne diseases.

The COVID-19 pandemic has highlighted the value of sterilizing both air that a user will inhale, and air a user has exhaled. By sanitizing both air streams, the user avoids infection from surrounding air, and surrounding third-parties avoid contracting airborne diseases from the user.

Ideally such a sterilizing device is portable, allowing a user to wear it in any setting, from a hospital to a grocery store.

Given that the sterilizing device needs to be worn at all times of day and in various locations, an integrated light is helpful to the user.

What is needed is a portable air sterilization device with integrated lighting.

SUMMARY

The sterilization mask with UVC reflective chamber includes a chamber with reflective liner, through which inhaled and exhaled air passes. The reflective chamber is also referred to as a sterilization chamber.

Using a reflective chamber ensures each photon of UVC light has a long life, thus dissipating slowly. Increasing the life of the UVC photons decreases the quantity of photons that must be created. Thus, less power is required to achieve the sterilization.

In addition to the internal light sources for sterilization, external outward-facing light sources provide indication of breathing, and/or external visible lighting to take the place of a headlamp. The position of the external light at the face of the mask, the mask worn over the mouth and nose, places the light closer to the relevant work surface to avoid shadowing and increase like intensity.

Sterilization is defined as a 6-log reduction (99.9999%) of various microbes including viruses, bacteria, and spores.

The reflective chamber is made reflective using a UVC internal reflective surface. This surface is preferably formed from ePTFE, or other equivalently UVC reflective material.

The use of ePTFE is ideal because it is 95% reflective in the frequency of UVC light. Thus, a single UVC photon can bounce twelve times before dissipating. As compared to a surface with no reflectivity, only 1/12 as much UVC light is needed to accomplish the same level of UVC concentration.

Other materials, such as aluminum, have only a 70% reflectance at best, thus losing 30% of the UVC energy at each bounce.

With the UVC light providing sterilization, the remaining requirement for air cleaning is particle filtration. This is accomplished using one or more filters. For example, pre-filters for large dust particles and aerosols. Air may also be filtered through stainless-steel cup filters that remove larger particles.

While filtration is important, it creates resistance to airflow. If this resistance is too high, such that the user perceives the resistance as an inability to breathe, it may result in panic and removal of the mask.

The solution is to create positive air pressure, compensating for the resistance of the filter.

In a first embodiment, the airflow is only in one direction, thus permitting a single fan to consistently push at the inlet, or pull at the outlet. But a fan that covers the entire inlet can create problems given the sinusoidal action of breathing. A fan that runs at a consistent speed will at times provide too much air, and too little at other times. Allowing the fan to increase and decrease speed can create unwanted noise.

Thus, a mechanical solution is ideal. In particular, discharging the fan through a perforated baffle. The holes, or perforations, in the baffle allow excess air to exit the system, or additional air to be drawn in. While fan may not keep up with peak air intake, it creates positive pressure and thus counteracts the resistance of the filter and increases user comfort.

As an alternative to a fan, the device may use the flow of warm air from the heatsink to create negative pressure at the air outlet. This helps to draw air out, thus helping the user to overcome the resistance of the filters. In summary, air that is warmed by the heatsink—the heat created by the device's electronics—is passed across the exhaust, pulling air out of the device.

Returning to sterilization, to further increase the effectiveness of UVC light sterilization, sonic agitation is optionally added to prevent shadowing.

To further reduce the UVC light quantity, and to prevent the escape of UVC light, the ends of the sterilization chamber are constructed as UVC trapping exits. Rather than escaping, any UVC light is either reflected back into the chamber or absorbed.

The action of trapping UVC light is accomplished by a mix of geometry and materials.

The geometry includes steep exit angles that prevent UVC photons from passing straight out. If photons bounce into the exit passage, they may encounter radial-angle deflectors that push photons back into the chamber.

If the photons avoid reflection, they will instead be absorbed by UVC absorbing material.

As an additional means of managing power consumption, the sterilization mask with UVC reflective chamber can adjust the UVC intensity depending on the user's breathing intensity and/or pattern.

Since airflow varies with both inhale and exhale, a continuous flux UVC system would need to irradiate enough UVC flux to achieve a 6-log reduction at the peak airflow rate. It is inefficient to sterilize at such an intensity when the air is static, such as between breaths, or during low-flow periods as breath increases or decreases. When the device is battery-powered, the result of over-consumption is reduced battery life and excessive heat production.

Using an airflow sensor, the device detects airflow, adjusting UVC flux to achieve sterilization but without excess power consumption. If a user's breathing rate exceeds sterilization capacity, an alarm sounds to alert the user that the air may not be fully sterilized.

In an alternative embodiment of the sterilization mask with UVC reflective chamber, the reflective chamber is divided to create unidirectional, or single-direction, air flow. This arrangement is an alternative to a bidirectional system, where inhaled and exhaled air pass back and forth through a single chamber. Bidirectional systems have the drawback of failing to fully exhaust all exhaled air, resulting in the next inhalation being warmer and with increased carbon dioxide.

But using two UVC chambers increases the size of a device, as well as complexity. Thus, this problem is best solved by using a single UVC chamber with two airways. Valves control the flow direction of the air, keeping the flow unidirectional. The two flow paths are separated by a UVC-transparent film, allowing a single set of UVC emitters to sterilize two separate flow paths.

Given that the device is worn in all situations, the integration of a light source increases usefulness. Additionally, the form factor of the system provides an opportunity to include a light at a position lower on the face than a typical headlamp.

A typical headlamp is placed on the user's forehead, requiring a band around the head, and placing the source of light further from any work surface onto which it is shining. Additionally, when combining a headline on the forehead with a face mask there is an increased chance of shadowing created by the protrusion of the face mask away from the face. Shadowing decreases the usefulness of the headlamp.

By integrating the light source into the face mask, the placement of the light source is lower. The face mask cannot create shadowing because the light is based on its external surface, and the light is closer to the work surface, decreasing the loss of light to the surroundings.

The light source emits light in the range of 100 nm to 950 nm, including ultraviolet, visible, and infrared wavelengths. The light source can be a single LED of fixed or varying wavelength, or an array of LEDs, with each LED of the array of LEDs having a fixed or varying wavelength.

The light has three operational modes controlled by an electronic control module. First, there is a simple on/off switch with four intensity setting options. Second, there is a breathing mode, referred to as breath pulsing mode, that dynamically increases and decreases the light intensity based on the wearer's breathing patterns, as measured by a pressure sensor. Third, there is a color mode that utilizes an array of LEDs of different wavelengths. The control module can activate certain LEDs to create specific color and wavelength combinations of light as desired.

A controller manages operation of the single LED or LED array to generate the required frequency or frequencies of light. The controller can adjust an intensity of emitted light created by the external light source—the single LED or LED array—where a higher intensity of emitted light matches a higher pressure sensor reading, and a lower intensity of light matches a lower pressure sensor reading. The result is the controller matching the light intensity to the breathing patterns of a user.

In summary, the light source provides wide-spectrum, hands-free lighting, with the option of dynamic breathing-synchronized patterns and selectable colors and wavelengths.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
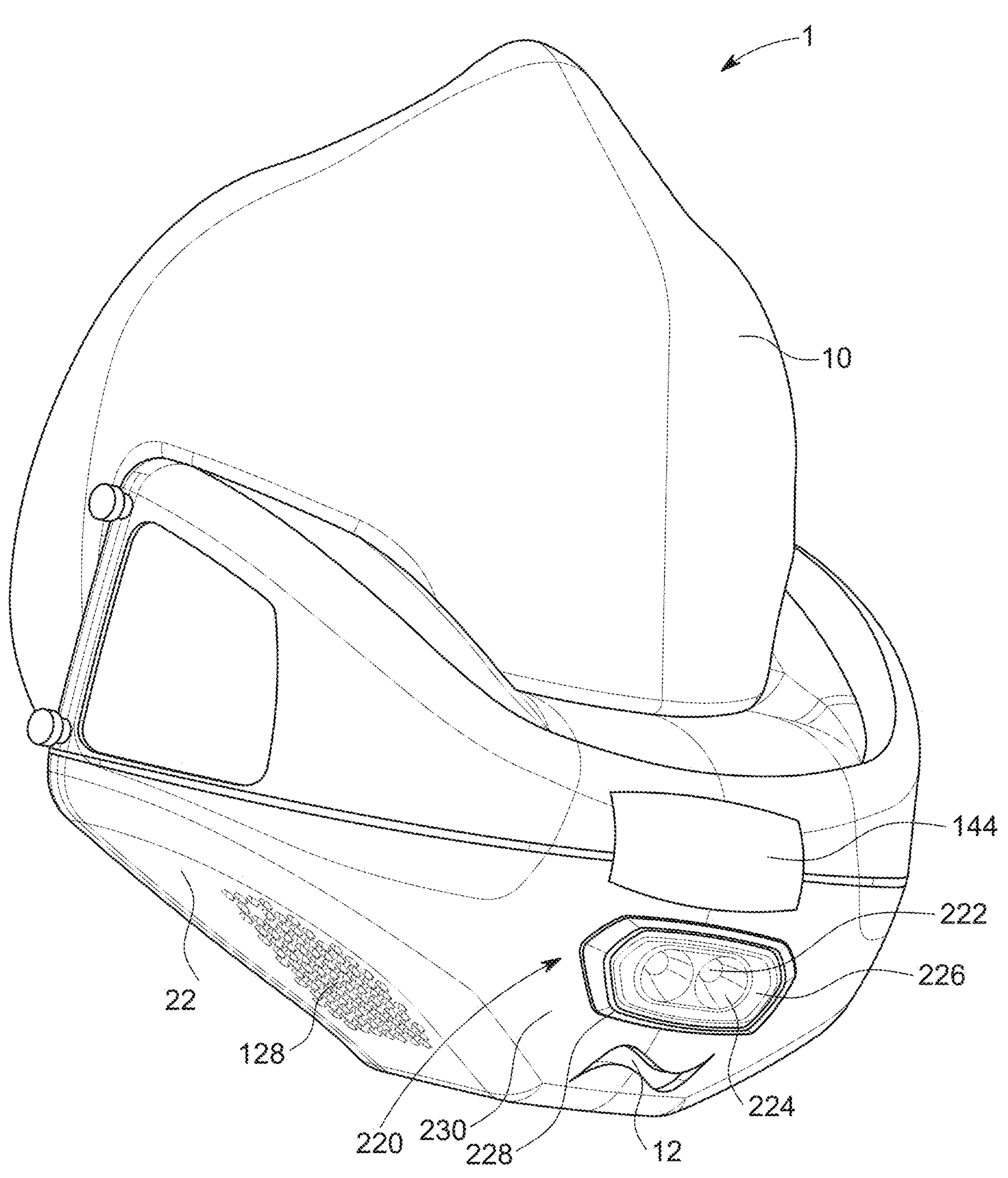
FIG. 1 illustrates a first isometric view of the sterilization mask with UVC reflective chamber, showing the integrated light.

Reference will now be made in detail to the presently preferred embodiments of the invention, examples of which are illustrated in the accompanying drawings. Throughout the following detailed description, the same reference numerals refer to the same elements in all figures.

Figure 2:
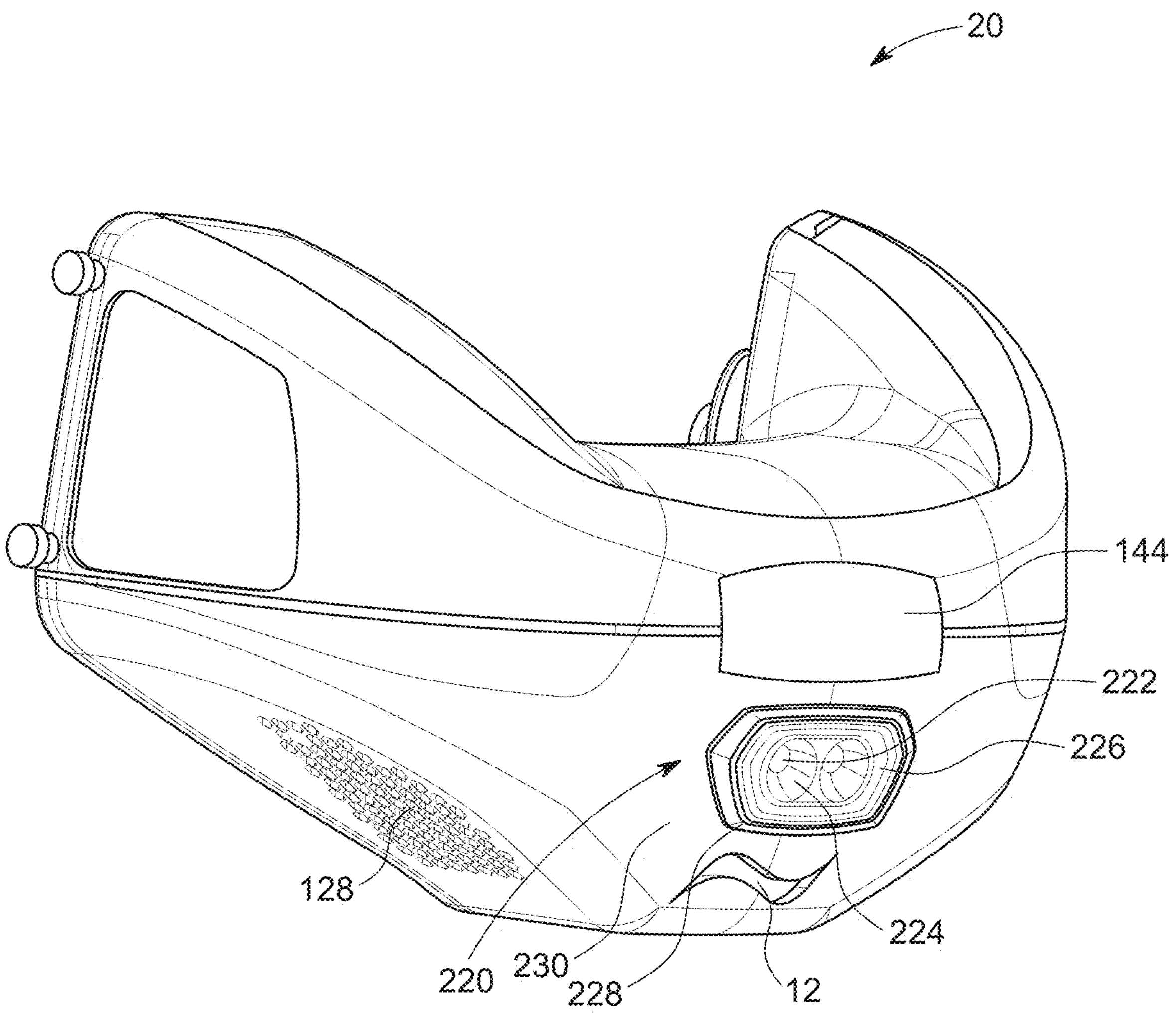
FIG. 2 illustrates a second isometric view of the sterilization module of the sterilization mask with UVC reflective chamber, showing the integrated light.

Referring to FIGS. 1 and 2, a first and second isometric view of the sterilization mask with UVC reflective chamber are shown.

The sterilization mask with UVC reflective chamber 1 is shown formed from primary components of the flexible mask 10 and the sterilization module 20.

Indicator light 12 activates to show that the sterilization mask with UVC reflective chamber 1 is operating.

Excess heat from operation is exhausted through warm air outlet 128.

The integrated light 220 is formed from an LED 222 sitting at the base of a reflector 224, covered with a clear cover 226 for protection.

The housing is formed from a front housing half 228 and a rear housing half 230. The rear housing half 230 is integrated with the housing 22 of the sterilization module 20, resulting in the integrated light 220 being partially surrounded by the housing of the sterilization mask with UVC reflective chamber 1.

Also shown is speaker 144, where the user's voice is emitted.

Figure 3:
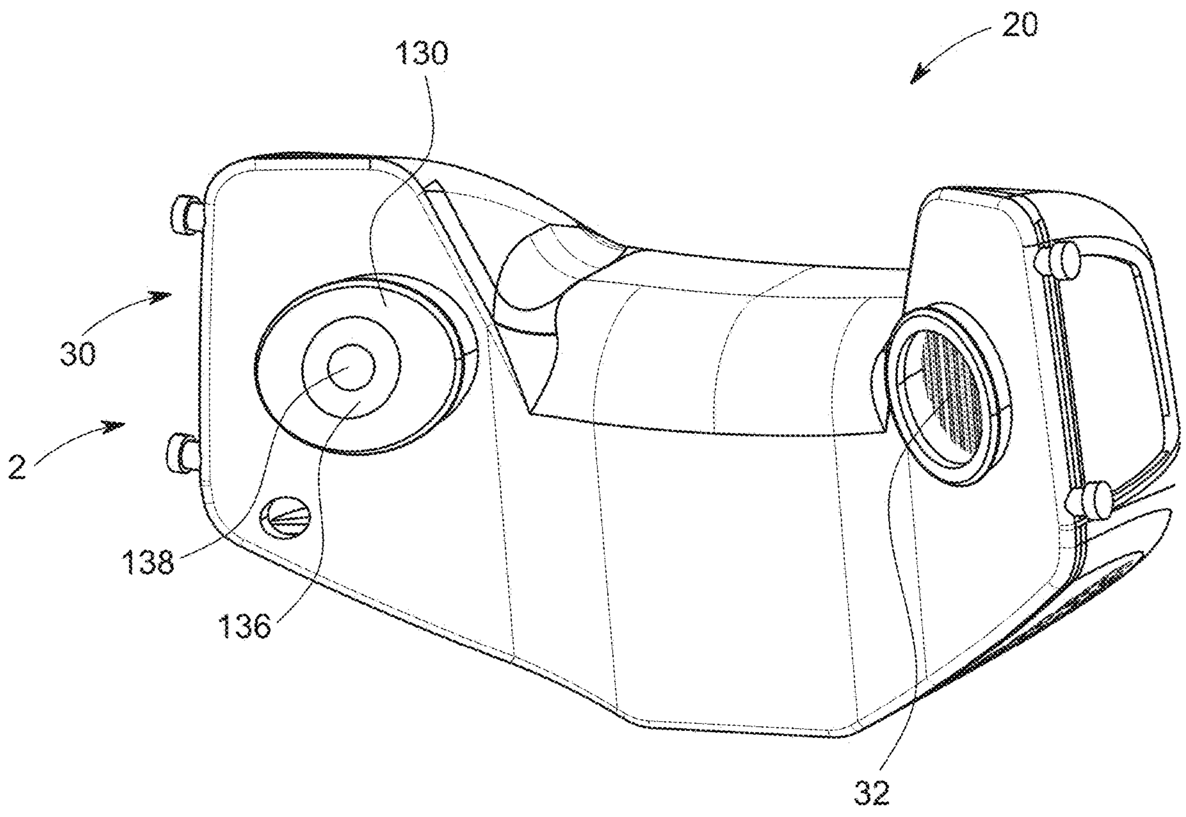
FIG. 3 illustrates a rear isometric view of the sterilization module of the sterilization mask with UVC reflective chamber.

Referring to FIG. 3, a rear isometric view of the sterilization module of the sterilization mask with UVC reflective chamber is shown.

As the user breathes in, the sterilization module 20 takes in air 2 via the atmospheric inlet/outlet 30, which is sterilized and passed to the user through the mask inlet/outlet 32. The reverse occurs as the user breathes out.

Also shown the exterior of audio components 130, including membrane 136 and hole 138.

Figure 4:
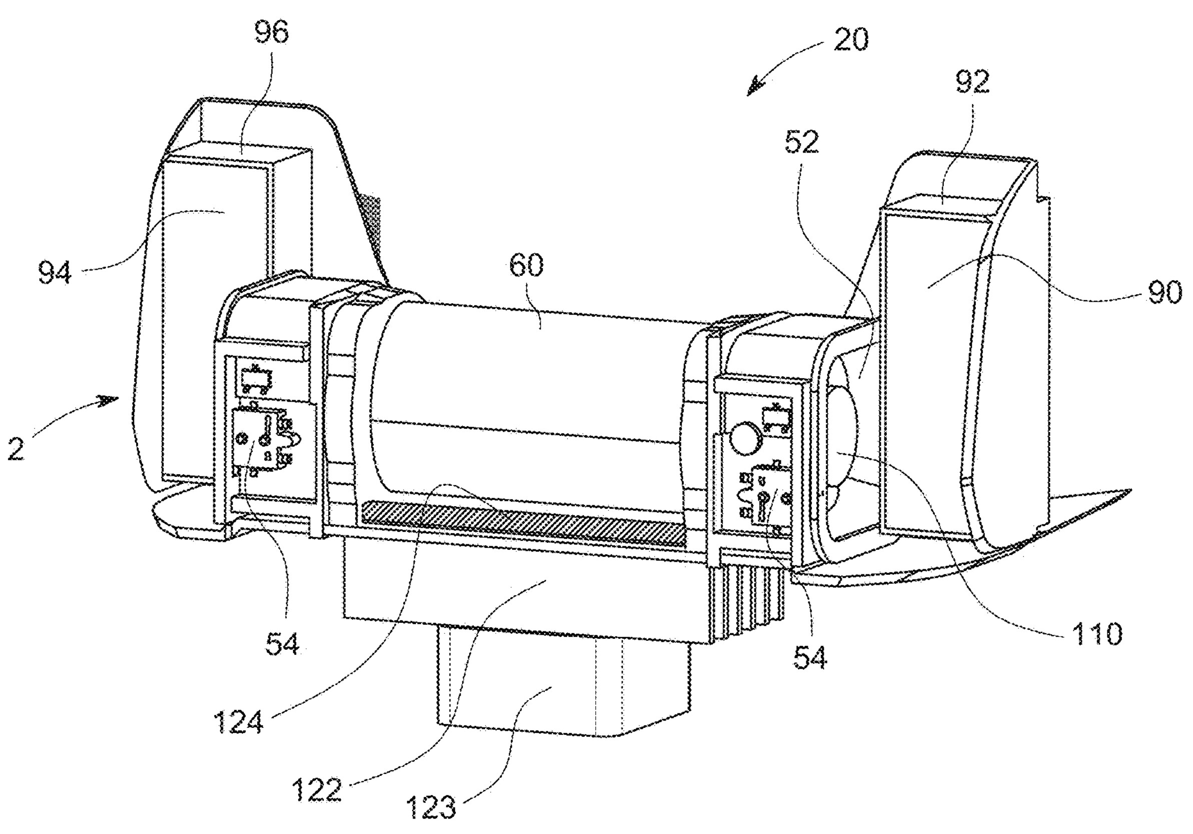
FIG. 4 illustrates an interior view of the sterilization module of the sterilization mask with UVC reflective chamber.

Referring to FIG. 4, an interior view of the sterilization module of the sterilization mask with UVC reflective chamber is shown.

The interior of the sterilization module 20 includes first filter 90 held within first filter holder 92, and second filter 94 held within second filter holder 96.

The filters 90/94 act to prefilter incoming air whether incoming from the atmosphere or from within the mask, i.e., from the user's exhalations.

Stainless steel screens 52 on each end of the reflective chamber 60 further filter the air 2. The presence of the stainless-steel screens 52 is monitored by the screen monitoring switches 54, which trigger an alarm if a screen 52 is missing.

After filtering, air 2 passes through the reflective chamber 60 wherein it is sterilized.

A heat sink 122 rests in contact with the aluminum UVC circuit board 124, drawing heat away. A heat sink fan 123 brings in outside air to cool the heat sink 122.

Figure 5:
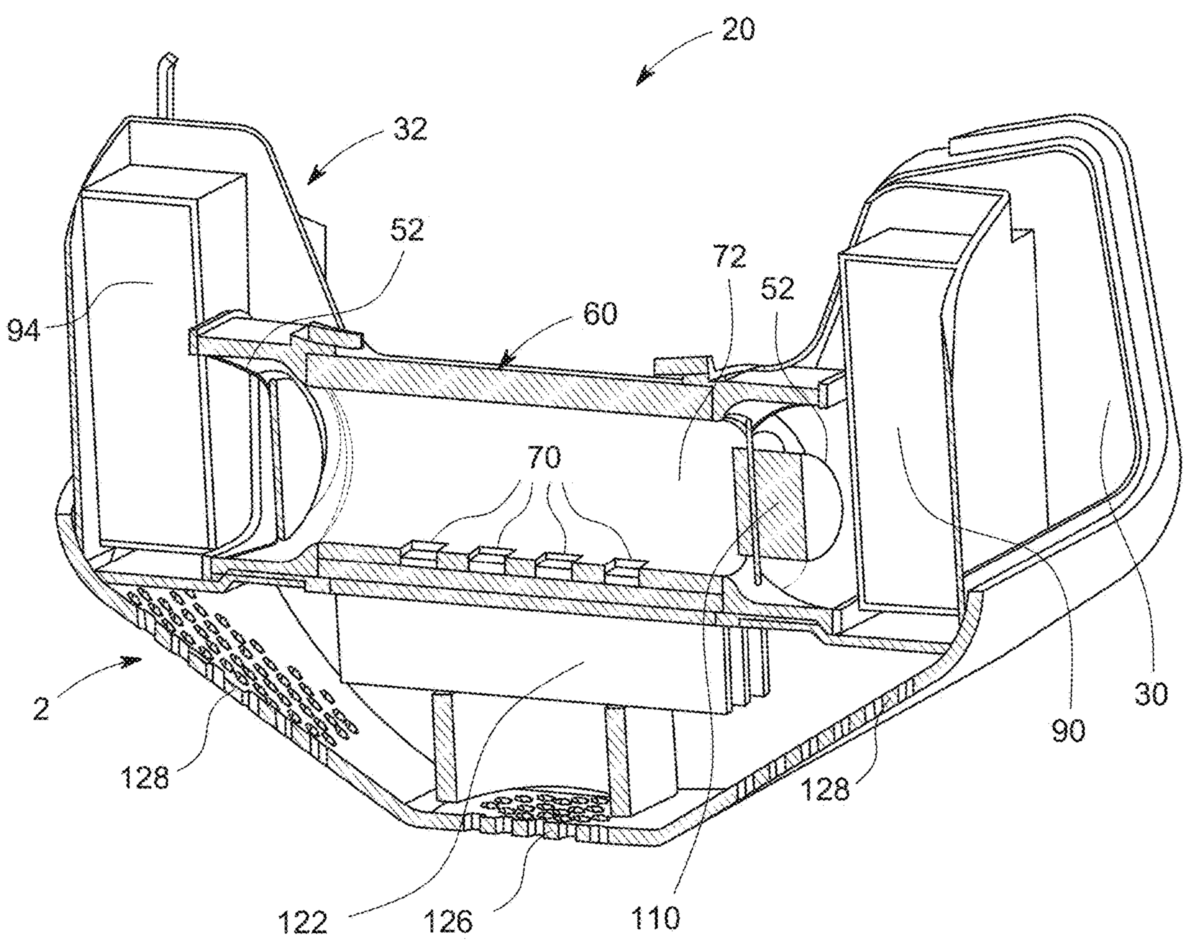
FIG. 5 illustrates a cutaway view of the rear of the sterilization module of the sterilization mask with UVC reflective chamber.
Figure 6:
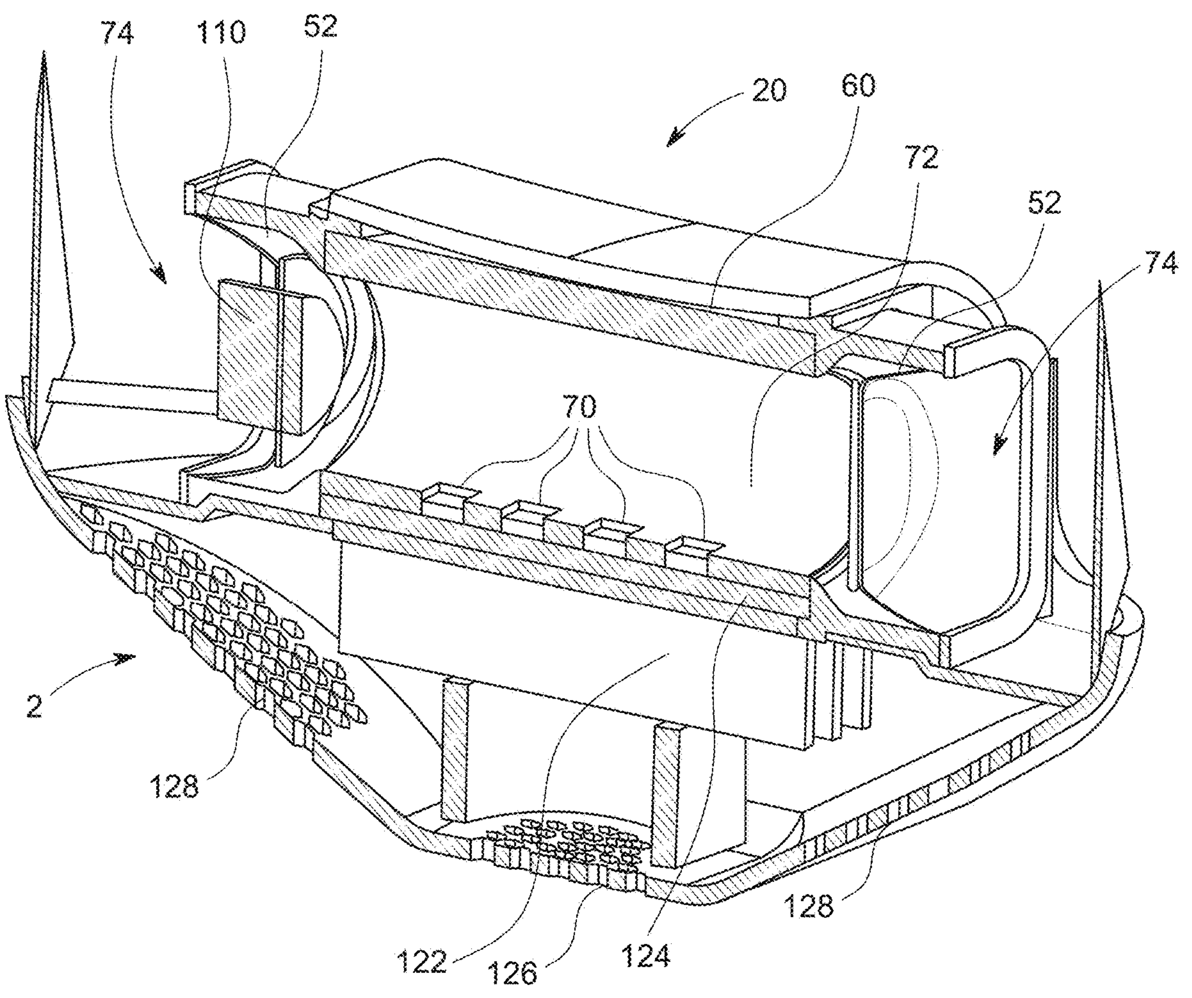
FIG. 6 illustrates a cutaway view of the front of the sterilization module of the sterilization mask with UVC reflective chamber.

Referring to FIGS. 5 and 6, cutaway views of the rear and front of the sterilization module of the sterilization mask with UVC reflective chamber are shown.

The sterilization module 20 is shown with reflective chamber 60, within which are the UVC emitters 70 that emit light against the UVC reflective interior surface 72.

The reflective chamber 60 ends in UVC trapping exits 74 that prevent the escape of UVC light.

A stainless-steel screen 52 sits at each end of the reflective chamber 60, filtering any air 2 entering the reflective chamber 60.

Also shown are the heat sink 122, cooled by air 2 passing into the cooling air inlet 126, and out the warm air outlet 128.

Figure 7:
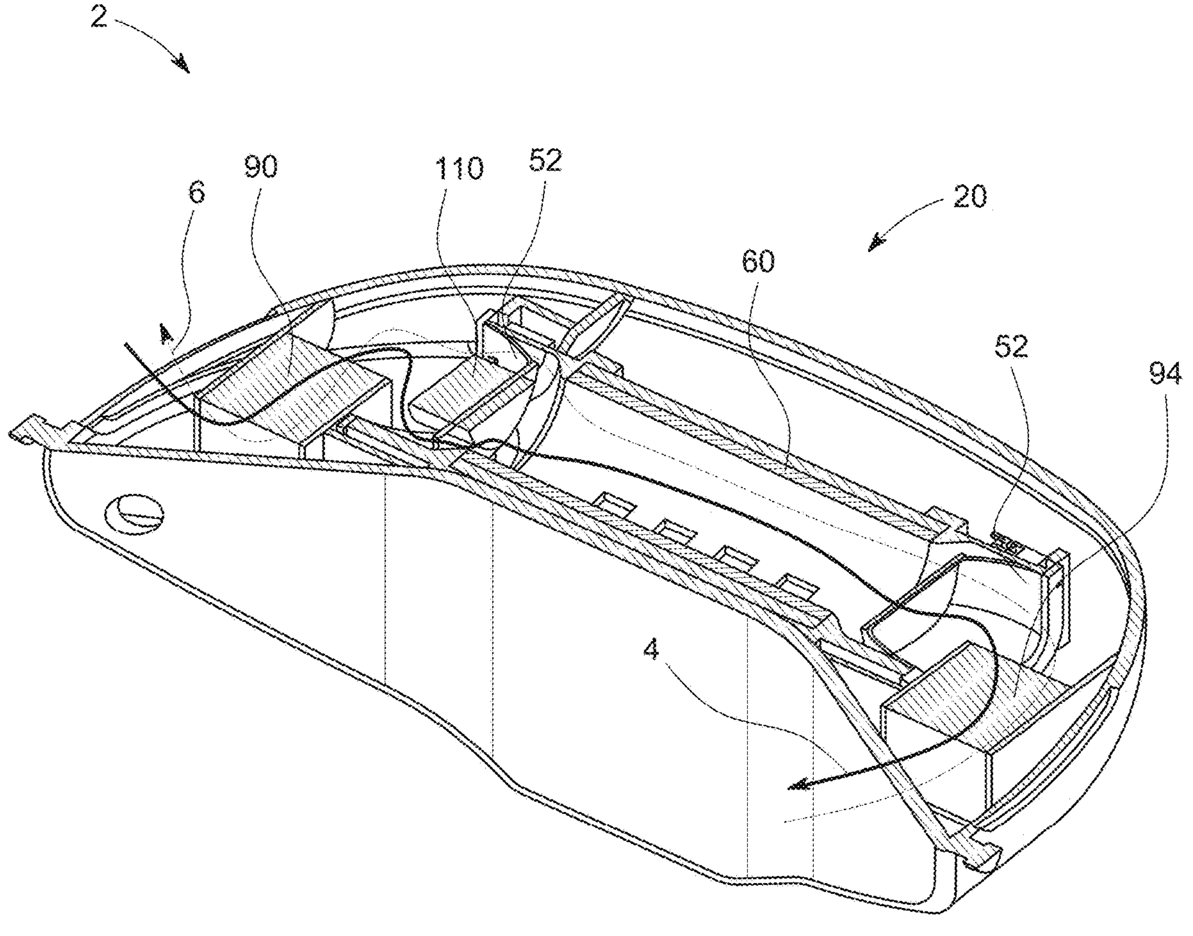
FIG. 7 illustrates a lower cutaway view of the sterilization module of the sterilization mask with UVC reflective chamber.
Figure 8:
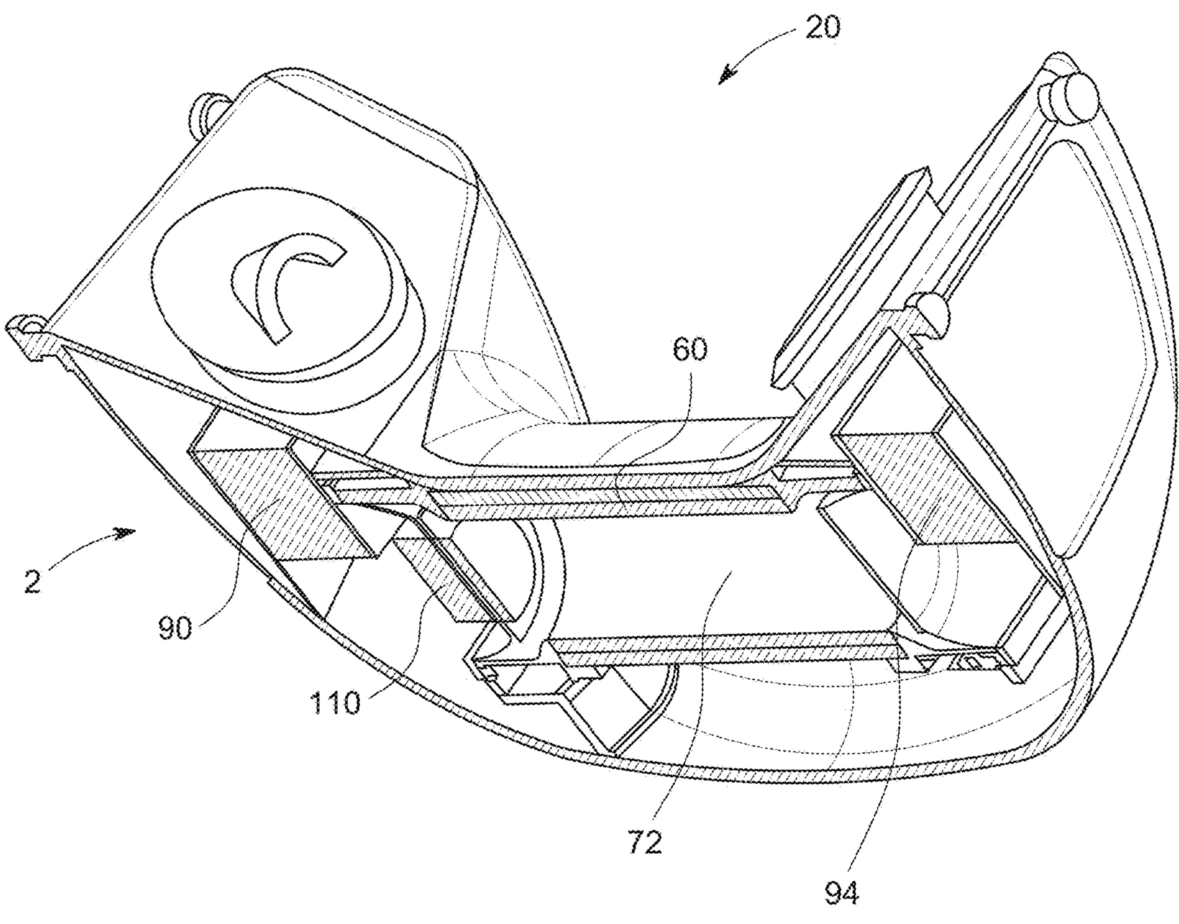
FIG. 8 illustrates an upper cutaway view of the sterilization module of the sterilization mask with UVC reflective chamber.

Referring to FIGS. 7 and 8, a lower cutaway view and an upper cutaway view of the sterilization module of the sterilization mask with UVC reflective chamber are shown.

Air 2 follows the inhalation flow 4 during a user's inhalation, and exhalation flow 6 during an exhalation.

Both flows 4/6 pass through the first filter 90, stainless steel screen 52, reflective chamber 60, stainless steel screen 52, and second filter 94, passing through the elements in opposing directions.

The sonic agitator 110 is also visible, placed at one end of the reflective chamber 60. Alternative placement of the sonic agitator 110 is anticipated, so long as it may still move the air within the reflective chamber 60.

Figure 9:
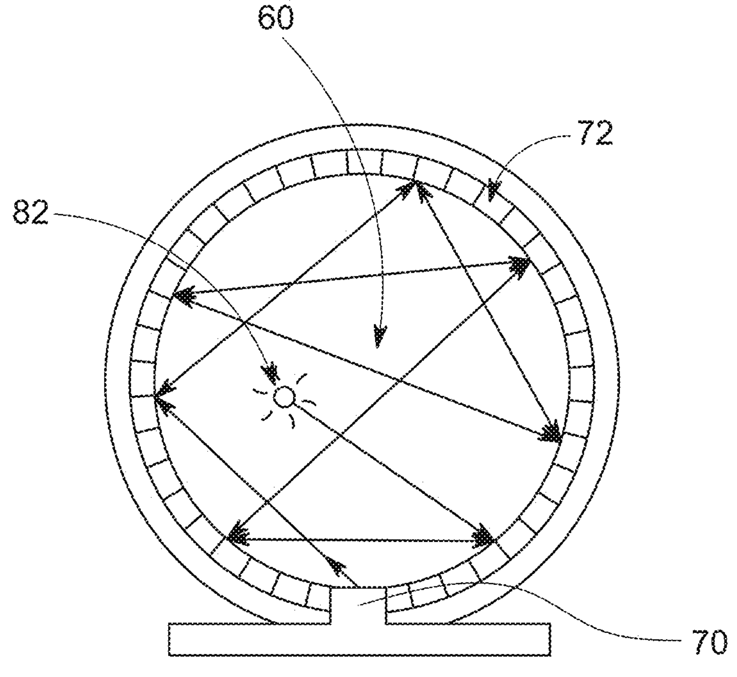
FIG. 9 illustrates a schematic view of the reflective chamber, in cross-section, of the sterilization mask with UVC reflective chamber.

Referring to FIG. 9, a schematic view of the reflective chamber, in cross-section, of the sterilization mask with UVC reflective chamber is shown.

The reflective chamber 60 includes one or more UVC emitters 70 that emit photons 82.

The photons 82 bounce inside the reflective chamber 60, reflected by the UVC reflective interior surface 72. The result of the highly-reflective UVC reflective interior surface 72 is that the photons 82 have a long life, and thus can sterilize larger volumes of air, thus lowering power consumption of the UVC emitters 70.

Figure 10:
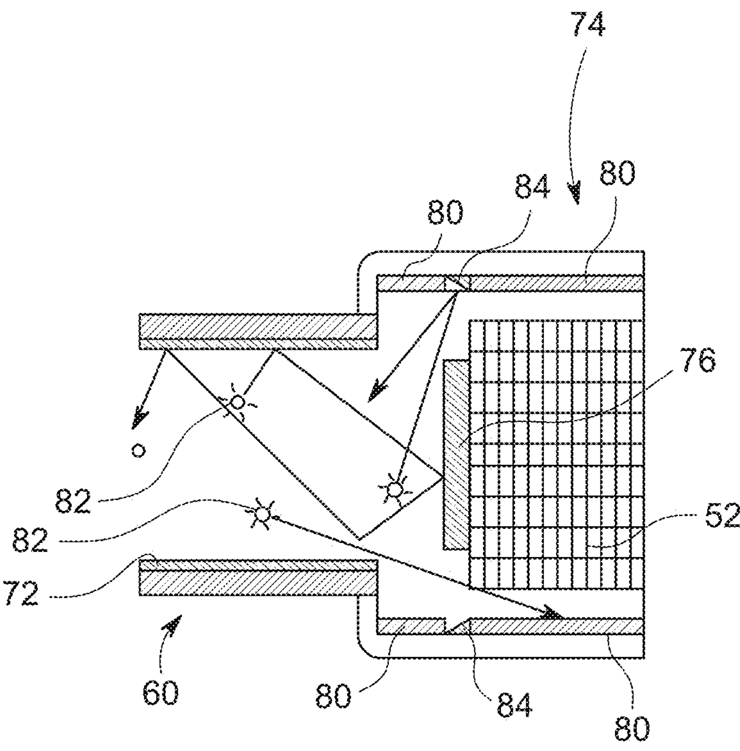
FIG. 10 illustrates a schematic view of an end, or UVC absorbing chamber, of the reflective chamber, of the sterilization mask with UVC reflective chamber.

Referring to FIG. 10, a schematic view of an end of the reflective chamber, of the sterilization mask with UVC reflective chamber is shown.

The UVC trapping exit 74 is shown with multiple features to prevent the escape of photons 82.

As photons 82 bounce around the reflective chamber 60, reflected by the UVC reflective interior surface 72, they reach the UVC trapping exit 74.

The centrally-mounted stainless steel screen 52 leaves space around the perimeter for air to exit. By only allowing a perimeter exit, the photons 82 must have a high angle to exit, making reflecting and absorbing an easier task than with an open-ended chamber.

Photons 82 may contact the UVC reflective exit surface 76, bouncing back into the reflective chamber 60.

Or photons 82 may contact the UVC exit reflector 84, which is set at angle to bounce the photons 82 back into the reflective chamber 60.

If photons 82 pass the reflective features, they contact the UVC absorbent material 80 that consumes UVC light, preventing an exit.

Figure 11:
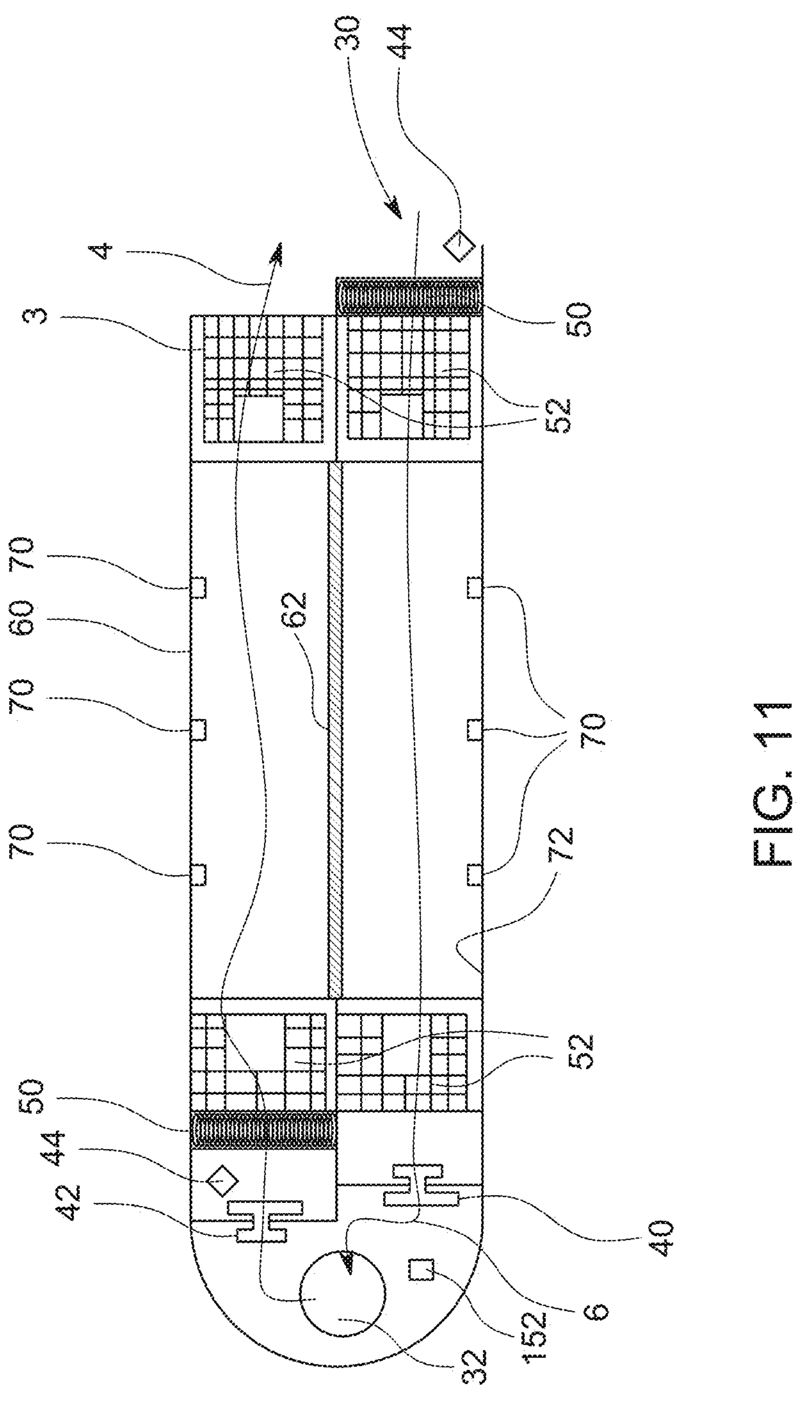
FIG. 11 illustrates a schematic view of a second embodiment of the reflective chamber, of the sterilization mask with UVC reflective chamber.

Referring to FIG. 11, a schematic view of a second embodiment of the reflective chamber, of the sterilization mask with UVC reflective chamber is shown.

The second embodiment includes two parallel flow paths for air through a single reflective chamber 60. This permits separate sterilization of incoming and outgoing air, without the requirement of two separate chambers.

Rather, a single chamber dividing wall 62 is placed across the reflective chamber 60, creating inhalation flow 4 and exhalation flow 6.

Air 2 enters from the atmosphere at the atmospheric inlet/outlet 30, entering the mask at the mask inlet/outlet 32, and then returning, but through the second half of the reflective chamber 60.

The inhalation valve 40 and exhalation valve 42 close during inhalation and exhalation respectively, ensuring air flows in the correct direction.

Incoming air passes through a prefilter element 50 to catch any particulates.

The flow meters 44 monitor inhalation flow 4 and exhalation flow 6, the volume of flow determining the intensity of the UVC emitters 70.

Also shown are the UVC emitters 70, UVC reflective interior surface 72, and stainless-steel screens 52.

Pressure sensor 152 is shown near mask inlet/outlet 32 where it senses the pressure of inhalation and exhalation. This pressure information is used to, among other things, control the operation of the integrated light 220 when in breath pulsing mode.

Figure 12:
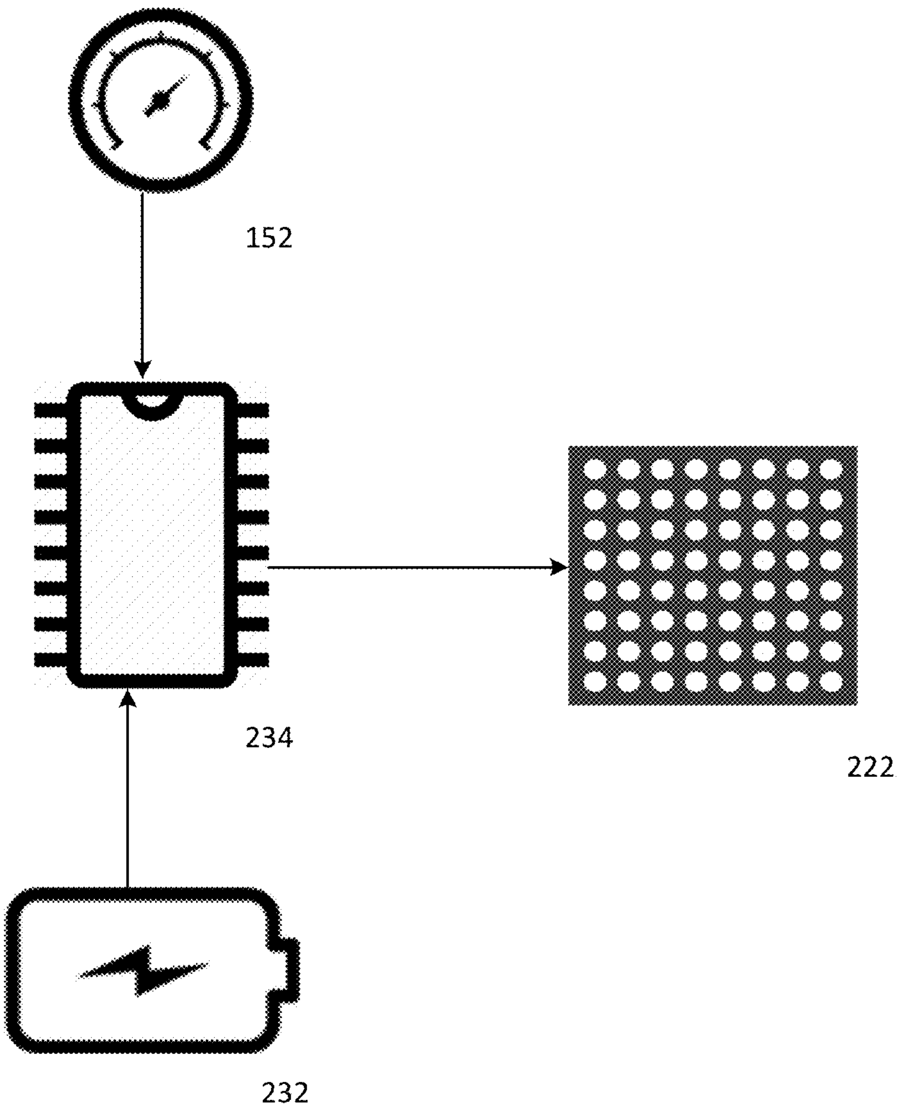
FIG. 12 illustrates a schematic view of the controller, pressure sensor, power source, and LED array of the sterilization mask with UVC reflective chamber.

Referring to FIG. 12, a schematic view of the controller, pressure sensor, power source, and LED array of the sterilization mask with UVC reflective chamber is shown.

The pressure sensor 152 sends pressure data to the controller 234, which in turn controls the LED or LED array 222. The system is powered by a power source 232, commonly a rechargeable battery.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A portable air sterilization device with integrated light comprising:
- a housing;
- a chamber;
  - the chamber within the housing;
  - the chamber including a mask connection point and an atmospheric connection point;
  - inhaled air and exhaled air passing in and out of the chamber via the mask connection point;
  - atmospheric air passing in and out of the chamber via the atmospheric connection point;
  - a chamber dividing wall that separates the chamber into a single-direction inhalation flow path and a single-direction exhalation flow path;
- a UVC reflective interior surface lining an inside of the chamber;
- one or more UVC light sources creating UVC light within the chamber;
  - the UVC light bouncing around an inside of the chamber by reflecting off the UVC reflective interior surface, thereby sterilizing the inhaled air and the exhaled air;
- an external light source integrated into the housing;
  - the housing partially surrounding the external light source;
  - the external light source including one or more LED emitters;
  - the external light source facing away from the chamber to light a surface beyond the portable air sterilization device;
- whereby a combination of the one or more UVC light sources and the one or more LED emitters sterilizes air internally while further emitting light externally.

2. The portable air sterilization device with integrated light of claim 1, wherein the external light source emits light between 100 nm to 950 nm.

3. The portable air sterilization device with integrated light of claim 1, wherein the external light source emits visible light between 380 nm to 750 nm.

4. The portable air sterilization device with integrated light of claim 1, further comprising:
- a pressure sensor;
  - the pressure sensor measuring whether a user is breathing in or out, and an intensity of breathing;
  - the pressure sensor outputting values based on a direction and the intensity of breathing;
- a controller;
  - the controller adjusting an intensity of emitted light created by the external light source, where a higher intensity of emitted light matches a higher pressure sensor reading, and a lower intensity of emitted light matches a lower pressure sensor reading;
- whereby the intensity of emitted light reflects the intensity of breathing.

5. The portable air sterilization device with integrated light of claim 2 further comprising:
- a pressure sensor;
  - the pressure sensor measuring whether a user is breathing in or out, and an intensity of breathing;
  - the pressure sensor outputting values based on a direction and the intensity of breathing;
- a controller;
  - the controller adjusting an intensity of emitted light created by the external light source, where a higher intensity of emitted light matches a higher pressure sensor reading, and a lower intensity of emitted light matches a lower pressure sensor reading;
- whereby the intensity of emitted light reflects the intensity of breathing.

6. The portable air sterilization device with integrated light of claim 1, wherein the external light source comprises an array of LEDs, the array of LEDs able to emit multiple wavelengths, thereby able to create a multitude of colors through a combination of wavelengths.

7. A portable air sterilization device with external lighting comprising:
- a housing;
- a chamber enclosed within the housing, the chamber having a mask connection point and an atmospheric connection point, wherein inhaled and exhaled air pass through the mask connection point and atmospheric air passes through the atmospheric connection point;
- a dividing wall within the chamber separating the chamber into a single-direction inhalation flow path and a single-direction exhalation flow path;
- one or more UVC light sources within the chamber creating UVC light that reflects off an interior UVC reflective surface of the chamber thereby sterilizing inhaled and exhaled air;
- an outward-facing light source integrated into the housing, wherein the housing partially surrounds the outward-facing light source, the outward-facing light source comprises one or more LED emitters facing away from the chamber in order to illuminate a surface beyond the portable air sterilization device;
- wherein a combination of the one or more UVC light sources within the chamber and the outward-facing light source integrated in the housing provides both internal air sterilization and external illumination.

8. The portable air sterilization device with external lighting of claim 7, wherein the outward-facing light source emits light between 100 nm to 950 nm.

9. The portable air sterilization device with external lighting of claim 7, wherein outward-facing light source emits visible light between 380 nm to 750 nm.

10. The portable air sterilization device with external lighting of claim 7, further comprising:
- a pressure sensor;
  - the pressure sensor measuring whether a user is breathing in or out, and an intensity of breathing;
  - the pressure sensor outputting values based on a direction and the intensity of breathing;
- a controller;

the controller adjusting an intensity of light created by the outward-facing light source, where a higher intensity of light matches a higher pressure sensor reading, and a lower intensity of light matches a lower pressure sensor reading;

whereby the intensity of light reflects the intensity of breathing.

11. The portable air sterilization device with external lighting of claim 8, further comprising:

a pressure sensor;

the pressure sensor measuring whether a user is breathing in or out, and an intensity of breathing;

the pressure sensor outputting values based on a direction and the intensity of breathing;

a controller;

the controller adjusting an intensity of light created by the outward-facing light source, where a higher intensity of light matches a higher pressure sensor reading, and a lower intensity of light matches a lower pressure sensor reading;

whereby the intensity of light reflects the intensity of breathing.

12. The portable air sterilization device with external lighting of claim 7, wherein the outward-facing light source comprises an array of LEDs, the array of LEDs able to emit multiple wavelengths, thereby able to create a multitude of colors through a combination of wavelengths.

13. A portable air sterilization device with internal and external lighting, the portable air sterilization device comprising:

a housing;

a chamber enclosed within the housing, the chamber having a mask connection point and an atmospheric connection point, wherein inhaled and exhaled air pass through the mask connection point and atmospheric air passes through the atmospheric connection point;

a dividing wall within the chamber separating the chamber into a single-direction inhalation flow path and a single-direction exhalation flow path;

one or more UVC light sources within the chamber creating UVC light that reflects off an interior UVC reflective surface of the chamber thereby sterilizing inhaled and exhaled air;

an outward-facing light source integrated into the housing, wherein the housing partially surrounds the outward-facing light source, the outward-facing light source comprises one or more LED emitters facing away from the chamber in order to illuminate a surface beyond the portable air sterilization device;

the outward-facing light source emitting visible light between 380 nm to 750 nm;

a pressure sensor;

the pressure sensor measuring whether a user is breathing in or out, and an intensity of breathing;

the pressure sensor outputting values based on a direction and the intensity of breathing;

a controller;

the controller adjusting an intensity of emitted light created by the outward-facing light source, where a higher intensity of emitted light matches a higher pressure sensor reading, and a lower emitted intensity of light matches a lower pressure sensor reading;

whereby the intensity of emitted light reflects the intensity of breathing.

* * * * *